United States Patent
Rose et al.

(10) Patent No.: US 7,344,851 B2
(45) Date of Patent: Mar. 18, 2008

(54) ANTICANCER AGENTS BASED ON PREVENTION OF PROTEIN PRENYLATION

(75) Inventors: Seth D. Rose, Tempe, AZ (US); Steven R. Ottersberg, Tempe, AZ (US); Karl J. Okolotowicz, Goleta, CA (US); Dale E. Robinson, San Diego, CA (US); Rosemarie F. Hartman, Tempe, AZ (US); Scott Lefler, Tempe, AZ (US)

(73) Assignee: Arizona Biomedical Research Commission, Phoenix, AZ (US)

( * ) Notice: Subject to any disclaimer, the term of this patent is extended or adjusted under 35 U.S.C. 154(b) by 116 days.

(21) Appl. No.: 11/246,259

(22) Filed: Oct. 11, 2005

(65) Prior Publication Data

US 2006/0030624 A1 Feb. 9, 2006

Related U.S. Application Data

(62) Division of application No. 10/437,050, filed on May 14, 2003, now Pat. No. 7,012,097, which is a division of application No. 09/457,476, filed on Dec. 9, 1999, now Pat. No. 6,576,436.

(60) Provisional application No. 60/111,478, filed on Dec. 9, 1998.

(51) Int. Cl.
*C12Q 1/48* (2006.01)
(52) U.S. Cl. .......................... 435/15; 514/561
(58) Field of Classification Search ....................... 435/4
See application file for complete search history.

(56) References Cited

U.S. PATENT DOCUMENTS

| | | | |
|---|---|---|---|
| 5,321,053 | A | 6/1994 | Hino et al. |
| 5,504,212 | A | 4/1996 | de Solms et al. |
| 5,602,115 | A | 2/1997 | Nugent |
| 5,710,171 | A | 1/1998 | Dinsmore et al. |
| 5,780,437 | A | 7/1998 | Goulet et al. |
| 5,789,427 | A | 8/1998 | Chen et al. |
| 5,859,012 | A | 1/1999 | Dinsmore et al. |
| 5,886,046 | A | 3/1999 | Hirschmann et al. |
| 6,083,985 | A * | 7/2000 | Yonemoto et al. .......... 514/568 |
| 6,284,910 | B1 * | 9/2001 | Spielmann et al. ......... 558/152 |
| 6,407,071 | B1 | 6/2002 | Rubin |
| 6,576,436 | B1 * | 6/2003 | Rose et al. .................... 435/15 |

FOREIGN PATENT DOCUMENTS

EP 0 512 865 A2 * 11/1992

OTHER PUBLICATIONS

Yang W. et al. Advances in the Development of Farnesyltransferase Inhibitors. J of Cellular Biochemistry Supplement 27:12-19, 1997.*
Yonemoto M. et al. J-104,871, A Novel Farnesyltransferase Inhibitor . . . Molecular Pharmacology 54(1)1-7, 1998.*
Sohn et al. "Chemical Modification Studies of Yeast Farnesyl Protein Transferase" J. Biochem Mol. Biol. vol. 30, No. 4, pp. 280-284, Jul. 31, 1997.
Barnard et al. "Characterization of Liver Prenyl Transferase and its Inactivation by Phenylglyoxal Biochimica et Biophysica Acts." Feb. 22, 1980, vol. 617, No. 2, pp. 169-182.
Barnard et al. "Human Liver Prenyltransferase and its Characterization" Biochimica et Biophysica Acta. Sep. 15, 1981, vol. 661, No. 1, pp. 87-99.
Boivin et al. "Essential Arginine Residues in Isoprenylcysteine Protein Carboxyl Methyltransferase" Biochem. Cell Biol. 1977, vol. 75, No. 1, pp. 63-69.
Pande et al. (1980). Camphorquinone-10-sulfonic acid and derivatives; Convenient reagents for reversible modification of arginine residues. Proc. Natl. Acad. Sci. USA 77(2), pp. 895-899.
CAPLUS abstract (Acc No. 1970:520240), Schank et al. (1970). Alpha-hydroxy-beta-oxosulfones: Influence of conjugation and substitution effects. Chem. Ber. 103(10): pp. 3087-3092.
Mori et al. (1991). Preparative bioorganic chemistry. Synthesis 6: pp. 487-490.
Neidlein et al. (1996). Syntheses of 2,3-dioxoalkylphonates and other novel beta-ketophosphonates as well as of a phosphoinopyruvalhide. Helv. Chim. Acta 79(3): pp. 895-912.
Wedzicha et al. (1975). Concentrations of sulfonates derived from sulphite in certain foods. J. Sci. Fd. Agric. 26: pp. 327-335.
Renis H. Progress Antimicrobial Anticancer Chemother, Proc. Int. Congr. Chemother, 6th, 1970, Meeting Date 1969, vol. 2, 844-854.
Casey, P.J., Journal of Lipid Research, Biochemistry of protein prenylation, 1992, pp. 1731-1740, vol. 33.
Bos, J.L., Cancer Research, *ras* Oncogenes in Human Cancer, A Review[1], 1989, pp. 4682-4689, vol. 49.
Casey, P.J. et al., The Journal of Biological Chemistry, Protein Prenyltransferases, 1996, pp. 5289-5292, vol. 271.
Leonard, D.M., Journal of Medicinal Chemistry, Ras Farnesyltransferase: A New Therapeutic Target, 1997, pp. 2971-2990, vol. 40.
Gibbs, J.B. et al., Annu. Rev. Pharmacol. Toxicol. The Potential Of Farnesyltransferase Inhibitors As Cancer Chemotherapeutics[1], 1997, pp. 143-166, vol. 37.
Cassidy, P.B. et al., Journal of Am. Chemical Society, Transition State Analogs for Protein Farnesyltransferase, 1996, pp. 8761-8762, vol. 118.
Patel, D.V. et al., Journal Med. Chem., Hydroxamic Acid-Based Bisubstrate Analog Inhibitors of Ras Farnesyl Protein Transferase, 1996, pp. 4197-4210, vol. 39.
Sattler, I., et al., "Prenylation of RAS and Inhibitors of Prenyltransferases.", In Regulation of the RAS Signaling Network, H. Maruta and A.W. Burgess, eds., 1996, Chapter 4, Chapman & Halki, Austin, TX.

(Continued)

*Primary Examiner*—Ralph Gitomer
(74) *Attorney, Agent, or Firm*—Banner & Witcoff Ltd.

(57) ABSTRACT

Prenylating enzymes are involved in modifying oncoproteins, such as RAS, so that growth of neoplastic cells becomes uncontrolled. Inactivation of such enzymes can prevent uncontrolled growth. α-Dicarbonyl compounds can be used to covalently modify and thereby inactivate prenylating enzymes such as protein farnesyltransferase and protein geranylgeranyltransferase. The compounds can be designed to enhance affinity and/or specificity for a particular protein substrate.

31 Claims, 4 Drawing Sheets

OTHER PUBLICATIONS

Figure 1:
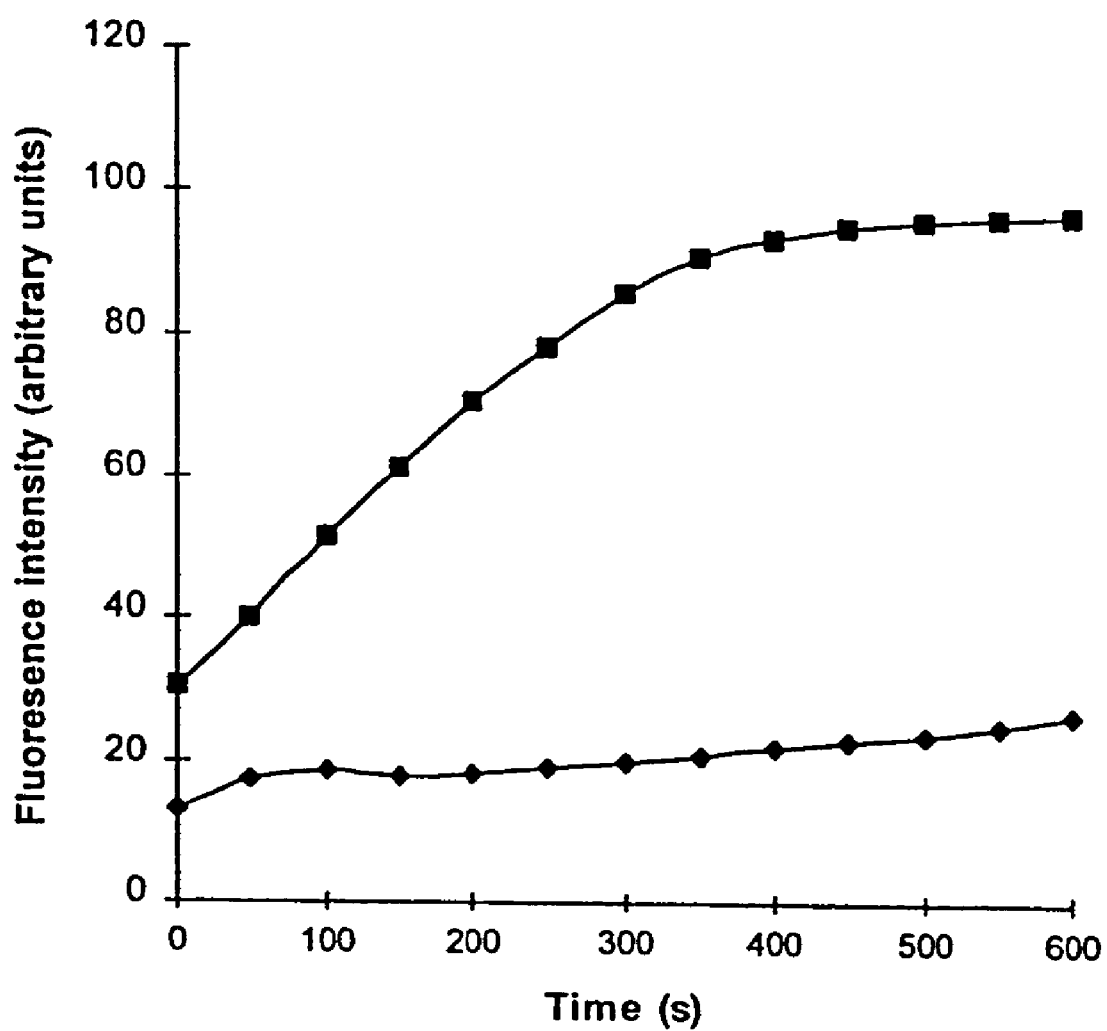

Huang, C.C., et al., The Journal Of Biological Chemistry, Evidence for a Catalytic Role of Zinc in Protein Farnesyltransferase, 1997, pp. 20-23, vol. 272.

Dolence, J.M., et al., Biochemistry, Yeast Protein Farnesyltransferase: Steady-State Kinetic Studies of Substrate Binding+, 1996, pp. 16687-16694, vol. 34.

Mu, Y.Q., et al., Journal of the American Chemical Society, On the Stereochemical Course of Human Protein-Farnesyl Transferase, 1996, pp. 1817-1823, vol. 118.

Park, H. W., et al., Science, Crystal Structure of Protein Farnesyltransferase at 2.25 Angstrom Resolution, 1997, pp. 1800-1804, vol. 275.

Dunten, P. et al., Biochemistry, Protein Farnesyltransferase: Structure and Implications for Substrate Binding, 1998, pp. 7907-7912, vol. 37.

Long, S.B., et al., Biochemistry, Cocrystal Structure of Protein Farnesyltransferase Complexed with a Farnesyl Diphosphate Substrate, 1998, pp. 9612-9618, vol. 37.

Takahashi, K., The Journal of Biological Chemistry, The Reaction of Phenylglyoxal with Arginine Residues in Proteins, 1968, pp. 6171-6179, vol. 243.

Pompliano, D.L., et al., J. Am. Chem. Soc., Intramolecular Fluorescence Enhancement: A Continuous Assay of Ras Farnesyl-Protein Transferase, 1992, pp. 7945-7946, vol. 114.

Patthy, L., et al., Eur. J. Biochem., Origin of the Selectivity of α-Dicarbonyl Reagents for Arginyl Residues of Anion-Binding Sites, 1980, pp. 387-393, vol. 105.

Rowell, C.A., et al., The Journal of Biological Chemistry, Direct Demonstration of Geranylgeranylation and Farnesylation of Ki-Ras in Vivo, 1997, pp. 14093-14097, vol. 272.

Whyte, D.B., et al., The Journal Of Biological Chemistry, K- and N-Ras Are Geranylgeranylated in Cells Treated with Farnesyl Protein Transferase Inhibitors, 1997, pp. 14459-14464, vol. 272.

Sattler, I. et al. Prenylation of RAS and Inhibitors of Prenyltransferases. Regulation of the RAS Signaling Network by Maruta and Burgess, R.G. Landes Co., Austin, TX, 1996.

Dedieu, M., C.R. Acad. Sc., Paris. vol. 282, Series C., pp. 65-67, 1976.

Stetter H. Synthesis. vol. 6, pp. 477-478, 1981.

Okolotowicz, K., Inactivation of Protein Farnesyltransferase by Active Site Targeted Dicarbonyl Compounds. Arch Pharm. Pharm. Med. Chem. 334(6)194-202, 2001.

* cited by examiner

ANTICANCER AGENTS BASED ON PREVENTION OF PROTEIN PRENYLATION

CROSS-REFERENCE TO RELATED APPLICATIONS

This application is a divisional of application Ser. No. 10/437,050, filed May 14, 2003, now U.S. Pat. No. 7,012,097, which is a divisional of application Ser. No. 09/457,476, filed Dec. 9, 1999, now U.S. Pat. No. 6,576,436, which claims benefit of provisional Application Ser. No. 60/111,478 filed Dec. 9, 1998. The disclosure of the provisional application is expressly incorporated by reference herein.

TECHNICAL FIELD OF THE INVENTION

This invention relates to the use of molecules with adjacent carbonyl groups (O=C—C=O), or related functional groups, that inactivate one or more prenyltransferases in cancer cells and thereby prevent the unrestrained division of cancer cells.

BACKGROUND OF THE INVENTION

More than half of all human cancers contain a mutant gene that encodes a mutant protein known as Ras. In cancer cells, Ras activates the cells to divide in an unrestrained manner. To induce cell division, Ras must be localized at the inner surface of the cancer cell membrane. Membrane localization of Ras is effected by attachment of a hydrophobic group, typically the farnesyl group, which becomes attached to Ras. In some cells, the related geranylgeranyl group becomes attached instead. Both of these groups become attached to Ras enzymatically, in a process known as prenylation. Thus, interference with prenylation of Ras has the potential to prevent Ras localization at the inner surface of the cancer cell membrane, resulting in the cessation of unrestrained cell division of the cancer cell.

The enzyme that attaches the farnesyl group to Ras protein to facilitate the latter's localization at the inner surface of the cancer cell membrane is farnesyl protein transferase, also known as protein farnesyltransferase (herein referred to as FTase). The farnesyl group becomes attached to Ras by reaction with farnesyl diphosphate, also known as farnesyl pyrophosphate (herein referred to as FPP). In other words, FTase catalyzes the following reaction, in which Ras becomes attached to the farnesyl group by displacement of pyrophosphate ($P_2O_7^{4-}$, herein referred to as $PP_i$):

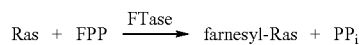

The newly formed farnesyl-Ras localizes at the inner surface of the cancer cell membrane and causes the cancer cell to divide without restraint.

There is a continuing need in the art for new ways to inhibit the growth of cancer cells. There is a need in the art for new ways to inactivate targets which are specifically involved in cancer progression and development.

SUMMARY OF INVENTION

It is an object of the invention to provide methods for inactivating prenylating enzymes.

It is another object of the invention to provide methods for screening test compounds for the ability to inactivate prenylating enzymes.

It is yet another object of the invention to provide methods for inhibiting the growth of a cancer cell.

It is still another object to provide pharmaceutical compositions for treating cancer.

It is another object to provide new compounds useful for treating cancers or inhibiting enzymes.

These and other objects of the invention are provided by one or more of the embodiments described below. In one embodiment a method of inactivating a prenylation enzyme is provided. The method comprises the step of contacting a prenylation enzyme with an α-dicarbonyl compound having formula (I): R1-(C=O)—(C=O)—R2, wherein R1 is selected from the group consisting of hydrogen, alkyl, alkenyl, alkynyl, and aryl; and wherein R2 is selected from the group consisting of hydrogen, alkyl, alkenyl, alkynyl, and aryl; and whereby the activity of the prenylation enzyme is reduced by at least 50%.

According to another embodiment of the invention, a method of screening compounds as anti-tumor agents is provided. The method comprises the step of contacting a test compound with a prenylation enzyme. The test compound has formula (I): R1-(C=O)—(C=O)—R2, wherein R1 is selected from the group consisting of hydrogen, alkyl, alkenyl, alkynyl, and aryl; and R2 is selected from the group consisting of hydrogen, alkyl, alkenyl, alkynyl, and aryl. Prenylation activity of the enzyme is measured. A test compound which reduces prenylation activity at least 50% is identified as a candidate anti-tumor agent.

According to another aspect of the invention a method of inactivating a prenylation enzyme is provided. The method comprises the step of contacting a prenylation enzyme with an α-dicarbonyl compound having formula (II): R1-(C=O)—(C=O)-L-(C=O)—(C=O)—R2, wherein R1, R2, and L are independently selected from the group consisting of hydrogen, alkyl, alkenyl, alkynyl, and aryl. The activity of the prenylation enzyme is reduced by at least 50%.

According to another aspect of the invention a method of screening compounds as anti-tumor agents is provided. A test compound is contacted with a prenylation enzyme. The test compound has formula (II): R1-(C=O)—(C=O)-L-(C=O)—(C=O)—R2, wherein R1, R2, and L are independently selected from the group consisting of hydrogen, alkyl, alkenyl, alkynyl, and aryl. Prenylation activity of the enzyme is measured. A test compound which reduces prenylation activity at least 50% is a candidate anti-tumor agent.

Another embodiment of the invention provides yet another method of inactivating a prenylation enzyme. A prenylation enzyme is contacted with an α-dicarbonyl compound having formula (III): A-L-D-R, wherein A is selected from the group consisting of an anionic group, a group that can spontaneously become anionic at physiological pH, and a group that can enzymatically become anionic at physiological pH; wherein L is a linker group; wherein D is a dicarbonyl functional group or a masked form of said group, and wherein R is selected from the group consisting of hydrogen, alkyl, alkenyl, alkynyl, and aryl. The activity of the prenylation enzyme is reduced by at least 50%.

Still another aspect of the invention is a method of screening compounds as anti-tumor agents. A test compound is contacted with a prenylation enzyme. The test compound has formula (III): A-L-D-R, wherein A is selected from the group consisting of an anionic group, a group that can spontaneously become anionic at physiological pH, and a group that can enzymatically become anionic at physiological pH; wherein L is a linker group; R is selected from the group consisting of hydrogen, alkyl, alkenyl, alkynyl, and aryl, and wherein D is a dicarbonyl functional group or a masked form of said group. Activity of the prenylation enzyme is measured. A test compound which reduces prenylation activity at least 50% is a candidate anti-tumor agent.

Also provided as an embodiment of the invention is a method of inhibiting growth of cancer cells. A cancer cell is contacted with an a-dicarbonyl compound having a formula: R1-(C=O)—(C=O)—R2. R1 is selected from the group consisting of hydrogen, alkyl, alkenyl, alkynyl, and aryl. R2 is selected from the group consisting of hydrogen, alkyl, alkenyl, alkynyl, and aryl. The growth of the cancer cell is consequently inhibited.

Another aspect of the invention is a method of inhibiting the growth of a cancer cell in which a cancer cell is contacted with an α-dicarbonyl compound having a formula: R1-(C=O)—(C=O)-L-(C=O)—(C=O)—R2. R1, L, and R2 are independently selected from the group consisting of hydrogen, alkyl, alkenyl, alkynyl, and aryl. The growth of the cancer cell is consequently inhibited.

Another embodiment of the invention is a method of inhibiting the growth of a cancer cell. A cancer cell is contacted with an α-dicarbonyl compound having a formula: A-L-D-R. A is selected from the group consisting of an anionic group, a group that can spontaneously become anionic at physiological pH, and a group that can enzymatically become anionic at physiological pH. L is a linker group, and R is selected from the group consisting of hydrogen, alkyl, alkenyl, alkynyl, and aryl. D is a dicarbonyl functional group or a masked form of said group. The growth of the cancer cell is consequently inhibited.

Also provided by the present invention is a pharmaceutically acceptable formulation. The formulation comprises a compound according to Formula I, Formula II, or Formula III, and a pharmaceutically acceptable excipient.

Additionaly provided by the present invention is a compound according to Formula I, Formula II, or Formula III. The compound is not phenylglyoxal, biphenyldiglyoxaldehyde, 2-oxododecanal, or 2,3-pentanedione.

The present invention thus provides a method for hampering or preventing the proliferation of cancer cells, resulting in a decrease in tumor size and/or disappearance of the cancer. It acts by interference with cancer cell biochemistry, in which the enzyme farnesyl protein transferase, geranylgeranyl protein transferase, and/or another prenylation enzyme acts on oncogenic proteins, such as RAS, or other growth-related cellular protein.

BRIEF DESCRCRIPTION OF THE DRAWINGS

FIG. 1. Assay of FTase after incubation of the enzyme in the absence (upper curve) and presence (lower curve) of inactivator (10 mM PGO for 10 min). Activity of human recombinant FTase was monitored by the increase in fluorescence at $\lambda=505$ nm, with farnesyl pyrophosphate and Ds-GCVLS (as a substitute for Ras) as substrates, after removal of PGO with a high molecular weight cutoff microconcentrator. The lower curve shows the virtual absence of enzyme activity following preincubation of FTase with PGO. Each point is the average of duplicate determinations.

Figure 2:
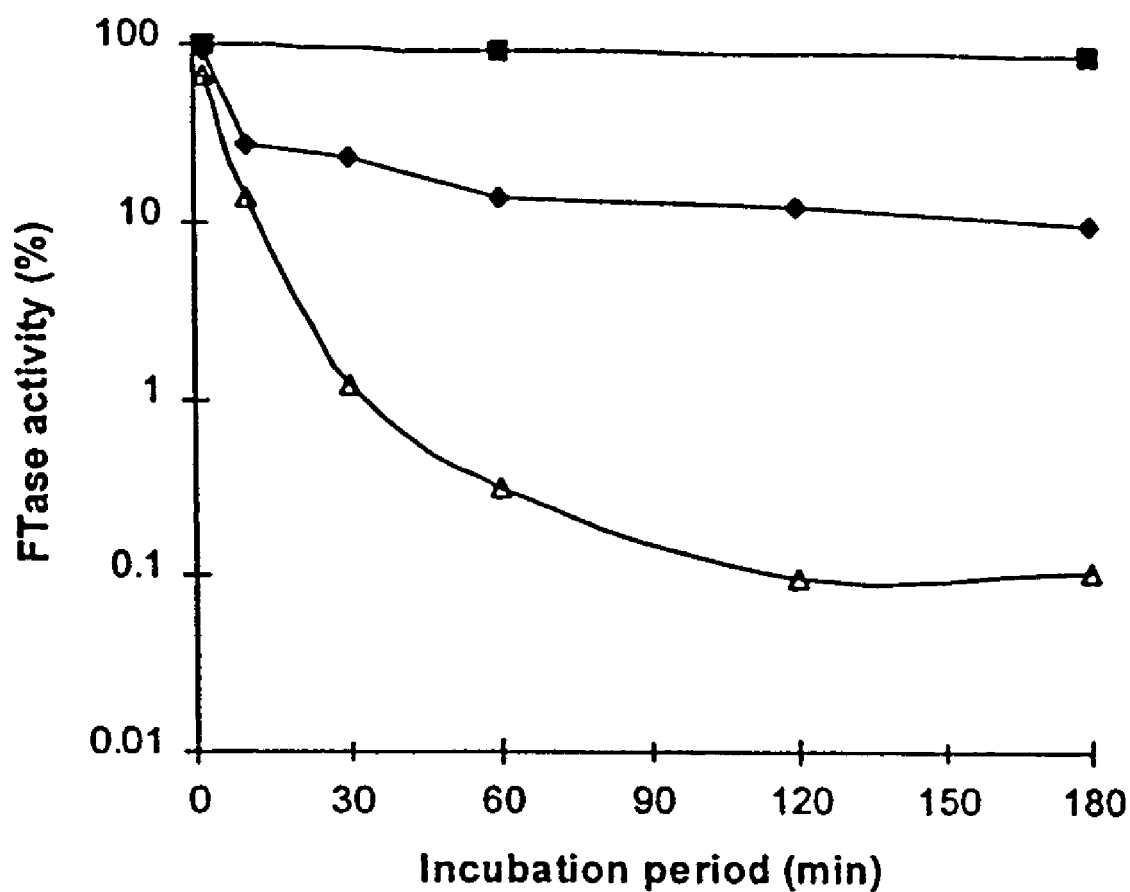

FIG. 2. Kinetics of inactivation of FTase by PGO. The rate of inactivation of FTase is dependent on PGO concentration. Loss of enzyme activity is faster at higher concentrations of PGO: (■) PGO absent, (♦) 5 mM PGO, and (Δ) 10 mM PGO. At 20 mM PGO, enzyme activity was lost in 2 min of incubation (data not shown). Assays were carried out after removal of PGO with a high molecular weight cutoff microconcentrator. Each point is the average of duplicate determinations.

Figure 3:
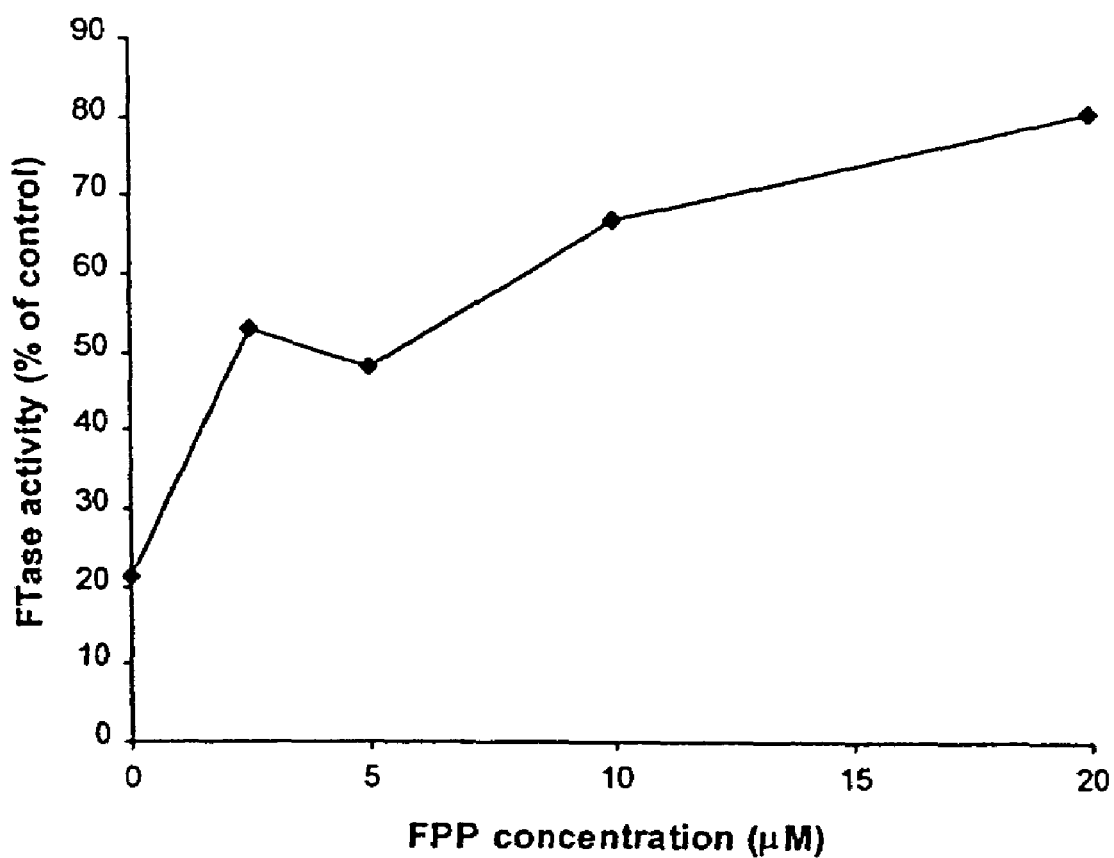

FIG. 3. Farnesyl pyrophosphate protection of FTase from inactivation by PGO. Points are determined by 100×(FTase activity after incubation with FPP and PGO)/(FTase activity after incubation with FPP without PGO). Assays were carried out after removal of FPP and PGO with a high molecular weight cutoff microconcentrator. Each point is the average of duplicate determinations.

Figure 4:
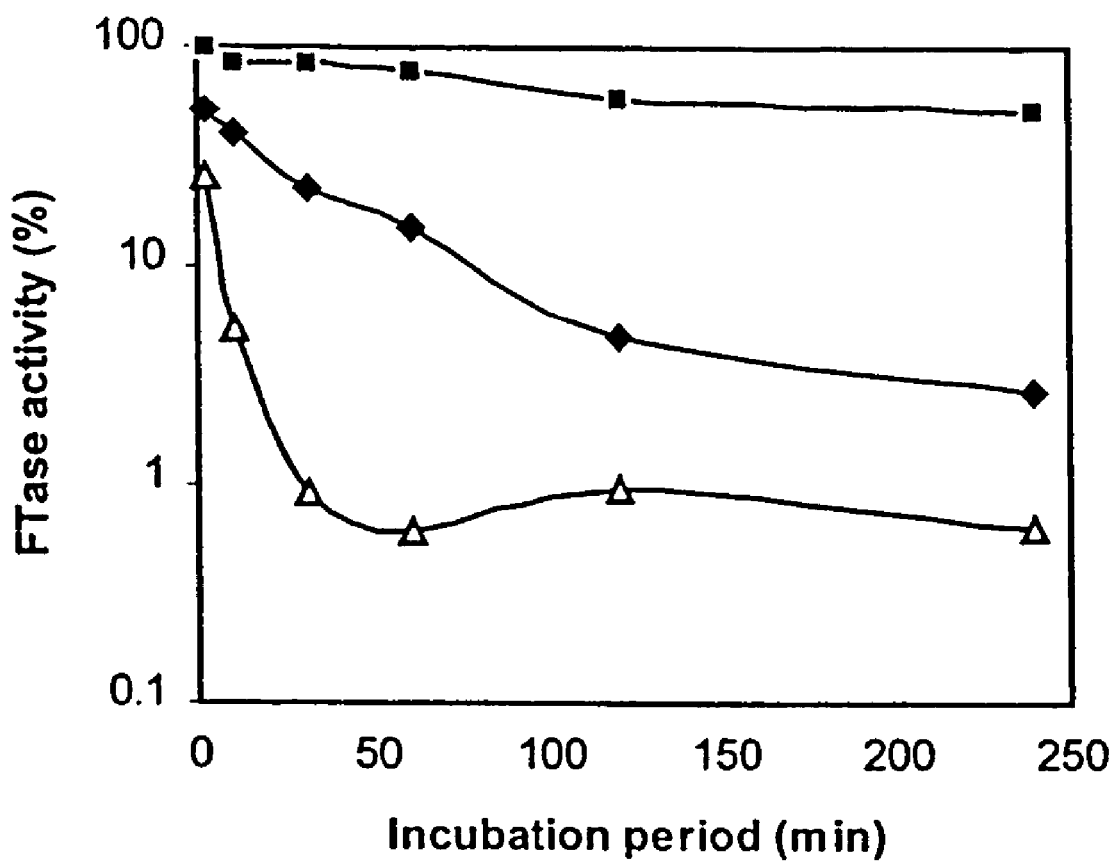

FIG. 4. Kinetics of inactivation of FTase by 2-oxododecanal. The rate of inactivation of FTase is dependent on 2-oxododecanal concentration. Loss of enzyme activity is faster at higher concentrations of 2-oxododecanal: (■) 2-oxododecanal absent, (♦) 5 mM 2-oxododecanal, and (Δ) 10 mM 2-oxododecanal. At 35 mM 2-oxododecanal, enzyme activity was lost in 2 min of incubation (data not shown). Dimethyl sulfoxide was present at 5% in the incubation mixtures (including the control). Assays were carried out after removal of 2-oxododecanal with a high molecular weight cutoff microconcentrator. Each point is the average of duplicate determinations.

DETAILED DESCRIPTION OF THE PREFERRED EMBODIMENTS

Key targets in a strategy to retard cancer cell proliferation are the prenylation enzymes, such as the enzyme FTase. By reducing or destroying FTase activity, we have found that we can prevent Ras farnesylation, which in turn prevents localization of Ras at the inner surface of the cancer cell membrane, thereby preventing Ras from causing the cancer cells to divide and proliferate.

Many substances are known to block FTase activity and prevent farnesylation of Ras. They consist of inhibitors of the enzyme FTase, and they generally operate by blocking the binding of Ras or FPP (or both) to FTase. Without the normal substrates (Ras and FPP) being able to bind to FTase, FTase cannot transfer the farnesyl group from FPP to Ras. Inhibitors structurally mimic one or both of the natural substrates of the enzyme, Ras and/or FPP. Their binding is noncovalent and reversible. In other words, the binding of the inhibitor to FTase does not involve the formation of covalent bonds between the inhibitor and FTase. Instead, hydrophobic forces, hydrogen bonding, electrostatic attraction, etc. are the forces principally responsible for binding of the inhibitor to the enzyme FTase. These binding forces allow the inhibitor to block the site on FTase where the normal substrates need to bind for farnesylation of Ras to take place.

We have found that a potentially more useful method of preventing FTase from farnesylating Ras can be achieved, namely inactivation of FTase. Interaction of FTase with substances that are inactivators results in the covalent attachment of a part or all of the inactivator to FTase. In principle, the covalent attachment can be irreversible or nearly irreversible. Also, the specificity of the inhibitor for the target enzyme FTase can be more finely tuned because it is based on two parameters: (1) structural similarity to the normal substrates (FPP and/or Ras); (2) a reactivity that is appropriate for the chemical groups that are a part of the enzyme FTase, particularly those that participate in the actual process catalyzed by FTase (i.e., those that more-or-less directly participate in the transfer of the farnesyl group of FPP to Ras).

The fact that FPP loses pyrophosphate, which is anionic, might be indicative of the presence of a structural feature in FTase that would assist in the displacement of pyrophosphate, for example by ionic bonding to a positively charged group in the enzyme's active site. One such possibility is the side chain of arginine [R—NH═C(NH$_2$)$_2$$^+$]. Indeed, the X-ray crystallographic structure determination of FTase reveals the presence of arginine residues in the vicinity of the hypothetical binding site of FPP, which further suggests the possible role of arginine in assisting with the removal of pyrophosphate as the farnesyl group becomes bonded to Ras.

Some chemical reagents that react with the side chain of arginine residues in proteins possess a functional group that comprises at least two adjacent carbonyl groups, i.e., O═C—C═O. Such a functional group binds covalently to the nitrogens of the side chain of arginine, causing the vicinity of the arginine to become blocked and possibly the positive charge to be lost. Hypothetical structures of the adduct(s) of the arginine side chain and the dicarbonyl compound phenylglyoxal are shown below:

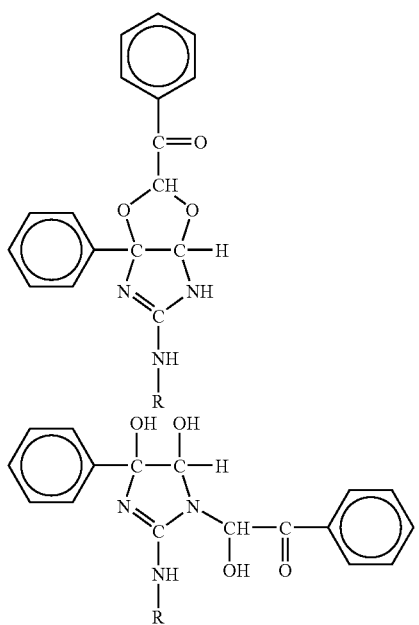

Our invention consists of chemical agents bearing at least two adjacent carbonyl groups (O═C—C═O) designed to react (i.e., covalently interact) with the arginine side chain. Furthermore, to target better the substance to FTase in preference to other enzymes, and to target better the substance to the active site of FTase in preference to the external or noncatalytic portion of the enzyme, a preferred embodiment of the invention consists of a substance with at least one dicarbonyl functional group and other structural features which favor the binding of the agent to the active site of FTase. For example, the active site of FTase is hydrophobic to bind the natural substrate FPP which contains a hydrophobic region (i.e., the farnesyl group). A hydrophobic substance that also contains the dicarbonyl functional group is preferred, a class represented by the following generalized structural formula:

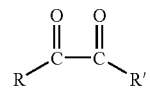

wherein R and R' represent hydrogen and/or a hydrophobic group, such as an alkyl, alkenyl, alkynyl, and aryl group. The group can be cyclic or noncyclic, branched or unbranched, with or without unsaturation (e.g., aryl, alkenyl) or substituents. Preferably the group is designed to impart specificity of the substance for binding to and/or inactivation of FTase.

The term "alkyl," as used alone or in combination herein, refers to an unsubstituted or optionally substituted, straight, or branched chain saturated hydrocarbon group containing from one to twenty-five carbon atoms, preferably from one to fifteen carbons, such as methyl, ethyl, n-propyl, n-butyl, pentyl, hexyl, heptyl, octyl, the various branch chain isomers thereof, such as isopropyl, isobutyl, sec-butyl, tert-butyl, isohexyl and the like. The alkyl group may be optionally substituted by one or more substituents, and generally no more than three, and most often just one substituent. Preferred optional substituents include halo, alkoxy, amino, mono- and di-substituted amino, aryl, carboxylic acid, heterocyclo, heteroaryl, cycloalkyl, hydroxy, trifluoromethoxy and the like. The term "lower alkyl" refers to such alkyl groups containing from one to five carbon atoms.

The term "alkoxy," as used alone or in combination herein, refers to an alkyl group, as defined above, covalently bonded to the parent molecule through an —O-linkage, such as methoxy, ethoxy, propoxy, isopropoxy, butoxy, t-butoxy and the like.

The term "alkoxyalkyl" refers specifically to an alkyl group substituted with an alkoxy group.

The term "aryloxy," as used alone or in combination herein, refers to an aryl group, as defined below, covalently bonded to the parent molecule through an —O-linkage. An example of an aryloxy is phenoxy.

The term "cycloalkoxy," as used alone or in combination herein, refers to a cycloalkyl group, as defined below, covalently bonded to the parent molecule through an —O-linkage.

The term "alkylthio," as used alone or in combination herein, refers to an alkyl group, as defined above, covalently bonded to the parent molecule through an —S-linkage.

The term "alkenyl," as used alone or in combination herein, refers to an alkyl group, as defined above, containing one or more carbon-carbon double bonds, preferably one or two double bonds. Examples of alkenyl include ethenyl, propenyl, 1,3-butadienyl, and 1,3,5-hexatrienyl.

The term "alkynyl," as used alone or in combination herein, refers to an alkyl group, as defined above, containing one or more carbon-carbon triple bonds, preferably one or two triple bonds.

The term "cycloalkyl," as used alone or in combination herein, refers to an unsubstituted or optionally substituted, saturated cyclic hydrocarbon group containing three to eight carbon atoms. The cycloalkyl group may optionally be substituted by one or more substituents, and generally no more than three, and most often just one substituent. Preferred optional substituents include alkyl, halo, amino, mono- and di-substituted amino, aryl, hydroxy and the like.

The term "haloalkyl" is a species of alkyl as defined herein, and particularly refers to an alkyl, preferably a lower alkyl, substituted with one or more halogen atoms, and preferably is a $C_1$ to $C_4$ alkyl substituted with one to three halogen atoms. One example of a haloalkyl is trifluoromethyl.

The term "alkanoyl" as used alone or in combination herein refers to an acyl radical derived from an alkanecarboxylic acid (alkyl-C(O)—), particularly a lower alkanecarboxylic acid, and includes such examples as acetyl, propionyl, butyryl, valeryl, and 4-methylvaleryl.

The term "aroyl" means an acyl radical derived from an aromatic carboxylic acid, such as optionally substituted benzoic or naphthoic acids and specifically including benzoyl and 1-naphthoyl.

The term "aminocarbonyl" means an amino-substituted carbonyl (carbamoyl or carboxamide) wherein the amino group is a primary amino (—$NH_2$). Substituted aminocarbonyl refers to secondary (mono-substituted amino) or tertiary amino (di-substituted amino) group, as defined below, preferably having as a substituent(s) a lower alkyl group.

The term "aminoalkanoyl" means an amino-substituted alkanoyl wherein the amino group is a primary amino group (-alkyl-C(O)—$NH_2$). The term "substituted aminoalkanoyl" refers to related secondary (mono-substituted amino) or tertiary amino (di-substituted amino) group, as defined below.

The term "carbocycloalkyl" when used alone or in combination refers to an unsubstituted or optionally substituted, stable, saturated or partially unsaturated monocyclic, bridged monocyclic, bicyclic, and spiro ring carbocycles of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. Cycloalkyls are thus one specific subset of carbocycloalkyls. The term "optionally substituted" as it refers to "carbocycloalkyl" herein indicates that the carbocycloalkyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkylamido (preferably lower alkylamido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Generally, there is no more than one optional substituent.

The term "heterocyclo" as used, alone or in combination, herein refers to an unsubstituted or optionally substituted, stable, saturated, or partially unsaturated, monocyclic, bridged monocyclic, bicyclic, and spiro ring system containing carbon atoms and other atoms selected from nitrogen, sulfur and/or oxygen. Preferably, a heterocyclo group is a 5 or 6-membered monocyclic ring or an 8-11 membered bicyclic ring which consists of carbon atoms and contains one, two, or three heteroatoms selected from nitrogen, oxygen and/or sulfur. Heterocyclo includes benz-fused monocyclic cycloalkyl groups having at least one such heteroatom. The term "optionally substituted" as it refers to "heterocyclo" herein indicates that the heterocyclo group may be substituted at one or more substitutable ring positions by one or more groups independently selected from alkyl (preferably lower alkyl and including haloalkyl (preferably trifluoromethyl)), alkoxy (preferably lower alkoxy), nitro, monoalkylamino (preferably a lower alkylamino), dialkylamino (preferably a di[lower]alkylamino), cyano, halo, alkanoyl, aminocarbonyl, monoalkylaminocarbonyl, dialkylaminocarbonyl, alkylamido (preferably lower alkylamido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Generally, there is no more than one optional substituent. Several non-limiting examples of such heterocyclo groups are illustrated below:

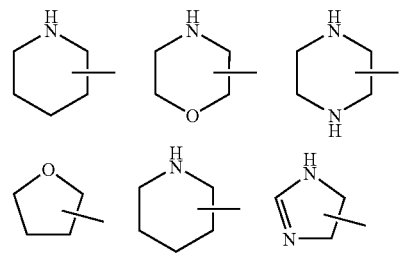

The heterocyclo group may be, and generally is attached to the parent structure through a carbon atom, or alternatively may be attached through any heteroatom of the heterocyclo group that results in a stable structure.

The term "heteroaryl" as used alone or in combination, herein refers to an unsubstituted or optionally substituted, stable, aromatic monocyclic or bicyclic ring system containing carbon atoms and other atoms selected from nitrogen, sulfur and/or oxygen. Preferably, a heteroaryl group is a 5- or 6-membered monocyclic ring (optionally benzofused) or an 8-11 membered bicyclic ring which consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (preferably lower alkyl and including haloalkyl (preferably trifluoromethyl)), alkoxy (preferably lower alkoxy), nitro, monoalkylamino (preferably a lower alkylamino), dialkylamino (preferably a di[lower]alkylamino, cyano, halo, alkanoyl, aminocarbonyl, monoalkylaminocarbonyl, dialkylaminocarbonyl, alkylamido (preferably lower alkylamido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Generally, there is no more than one optional substituent. Several non-limiting examples of such heteroaryl groups are illustrated below:

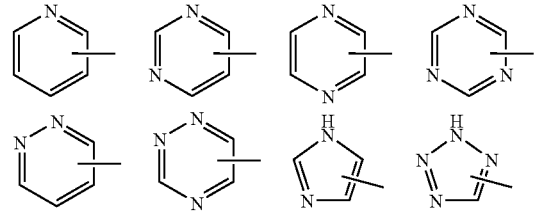

-continued

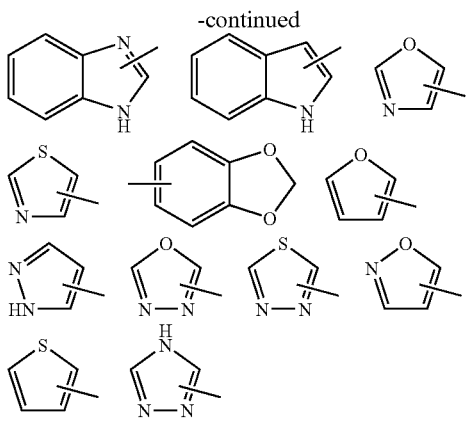

The heteroaryl group may be, and generally is attached to the parent structure through a carbon atom or alternatively may be attached through any heteroatom of the heteroaryl group that results in a stable structure. In the foregoing structures it also is contemplated that a nitrogen could be replaced with an N-oxide.

Both heterocyclo and heteroaryl also are intended to embrace benzo fused structures such as 1,2-methylenedioxybenzene and 1,4-benzodioxan.

The terms "halo" and "halogen" as used herein to identify substituent moieties, represent fluorine, chlorine, bromine or iodine, preferably chlorine or fluorine.

The term "aryl," when used alone or in combination, refers to an unsubstituted or optionally substituted monocyclic or bicyclic aromatic hydrocarbon ring system having 6 to 12 ring carbon atoms. Preferred are optionally substituted phenyl, 1-naphthyl, or 2-naphthyl groups. The aryl group may optionally be substituted at one or more substitutable ring positions (generally at no more than three positions and most often at one or two positions) by one or more groups independently selected from alkyl (including haloalkyl (preferably trifluoromethyl and difluoromethyl)), alkenyl, alkynyl, alkoxy, aryloxy, nitro, hydroxy, amino, mono- and di-substituted amino, cyano, halo, alkanoyl, aminocarbonyl, carboxylic acid, carboxylic acid esters, carboxylic acid amide, an optionally substituted phenyl (optionally substituted by halo, lower alkyl and lower alkoxy groups), heterocyclo, or heteroaryl. Preferably, the aryl group is phenyl optionally substituted with up to four and more usually with one or two groups, preferably selected from lower alkyl, lower alkoxy, as well as cyano, trifluoromethyl and halo.

The terms "aralkyl" and "(aryl)alkyl," alone or in combination are a species of alkyl as defined herein, and particularly refers to an alkyl group as defined above in which one hydrogen atom is replaced by an aryl group as defined above, and includes benzyl, and 2-phenylethyl.

The terms "(heterocyclo)alkyl" and "(heteroaryl)alkyl" alone or in combination can be considered a species of alkyl as defined herein, and particularly refers to an to an alkyl group as defined above in which one hydrogen atom is replaced by a heterocyclo group as defined above, or by a heteroaryl group as defined above.

The term "alkoxycarbonyl" alone or in combination means a radical of the formula —C(O)-alkoxy, in which alkoxy is as defined above.

The term "alkylcarbonyloxy" alone or in combination means a radical of the formula —O—C(O)-alkyl, in which alkyl is as defined above.

The term "alkoxyalkanoyl" alone or in combination means a radical of the formula-alkyl-C(O)—O-alkyl.

The term "carboxyalkyl" alone or in combination means a radical of the formula-alkyl-C(O)—OH.

The term "substituted amino" embraces both mono and di-substituted amino. These terms, alone, or in combination, mean a radical of the formula —NR$^1$R", where, in the case of mono-substitution, one of R' and R" is a hydrogen and the other is selected from alkyl, cycloalkyl, aryl, heterocyclo, (aryl)alkyl, (heterocyclo)alkyl, heteroaryl and hetero(aryl)alkyl; in the case of di-substitution, R' and R" are independently selected from alkyl, cycloallyl, aryl, heterocyclo, and heteroaryl, or R' and R" together with the nitrogen atom to which they are both attached form a three to eight-membered heterocyclo or heteroaryl radical.

The term "amido" refers to the group (—NH—) and the term "substituted amido" embraces a radical of the formula (—NR—) where R' has the meaning above in connection with substituted amino.

The terms "alkanoylamido," "aroylamido," "heterocyclocarbonylamido" and "heteroaroylamido" mean groups of the formula R—C(O)—NH— where R is an alkyl, aryl, heteroaryl or heterocyclo group.

The terms "heteroaroyl" and "heterocyclocarbonyl" when used alone or in combination means groups of the formula R—C(O)—where R is a heteroaryl or heterocyclo group.

Unless otherwise defined, the term "optionally substituted" as used herein, refers to the substitution of a ring system at one or more positions with one or more groups selected from: $C_{1-5}$ alkyl, $C_{1-5}$ alkoxy, an optionally substituted phenyl, cyano, halo, trifluoromethyl, $C_{1-5}$ alkoxycarbonyl, $C_{1-5}$ alkyl carbonyloxy, mono- and bis-($C_{1-5}$ alkyl)-carboxamide, $C_{1-5}$ alkylamido, nitro, and mono- and bis-($C_{1-5}$ alkyl)-amino.

Applicants recognize that there may be some overlap in some of the definitions of the various radical groups. Specific groups are mentioned, however, such as (aryl)alkyl, and may be particularly identified in the claims, in order to emphasize their positive inclusion in the described subject matter, as not only an optional substituent.

As used herein, when a particular radical generally understood to have a single point of attachment to a core structure, such as an alkyl group, is identified in connection with a structure that must have two points of attachment in the structural core (such as with the element L in formula (II)), it is understood that the named radical, e.g., alkyl, refers to the parent radical with a hydrogen or a site of unsaturation removed to create the second point of attachment so as to provide the required structure.

Anionic groups according to the present invention, designated as "A" herein, include carboxylate, sulfate, sulfonate, sulfinate, sulfonamides, sulfones, phosphate, phosphonate, phosphinate, tetrazoles, thiophosphate, pyrophosphate, enolate, or a precursor group that can be converted to an anionic group, either spontaneously or enzymatically in cells.

A specific embodiment of this invention is phenylglyoxal, shown below, although many other compounds that can achieve the desired effect are readily apparent to those skilled in the art, having regard for this disclosure:

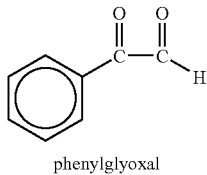

phenylglyoxal

Two additional categories of specific embodiments, in which an aliphatic chain is capable of binding to the active site of FTase by hydrophobic interactions, are defined as follows:

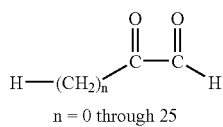

n = 0 through 25

2-oxoaldehydes
(e.g., 2-oxododecanal when n = 10, in EXAMPLE 2 below)

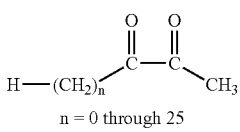

n = 0 through 25 alkanediones
(e.g., 2,3-tetradecanedione when n = 11)

Also, substances with complex substituents might be better mimics of the farnesyl group of the substrate FPP and function more effectively as inhibitors, as for example, the compounds below:

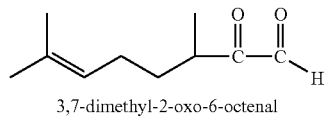

3,7-dimethyl-2-oxo-6-octenal

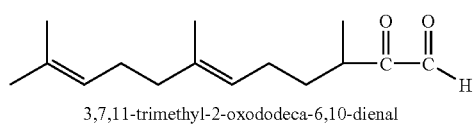

3,7,11-trimethyl-2-oxododeca-6,10-dienal

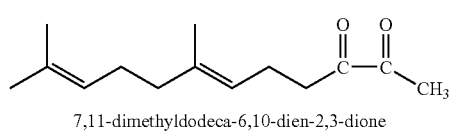

7,11-dimethyldodeca-6,10-dien-2,3-dione

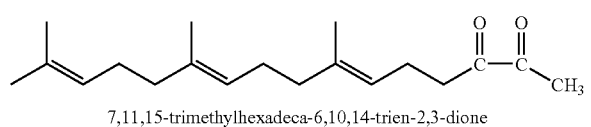

7,11,15-trimethylhexadeca-6,10,14-trien-2,3-dione

An additional compound that consists of the general formula R—(C=O)—(C=O)—R', or a masked form of such a group as denoted elsewhere in this application (e.g. acetal, ketal, etc.), and is contemplated by this disclosure is the following:

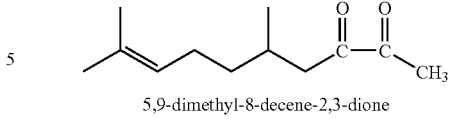

5,9-dimethyl-8-decene-2,3-dione

The synthesis of the above compound may be carried out as follows:

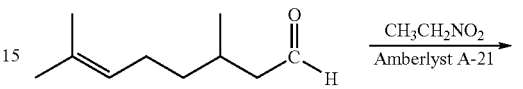

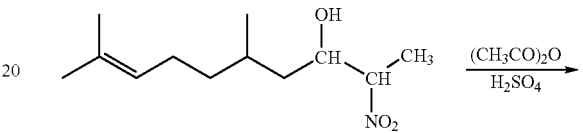

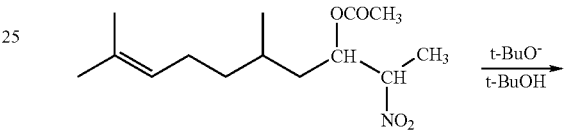

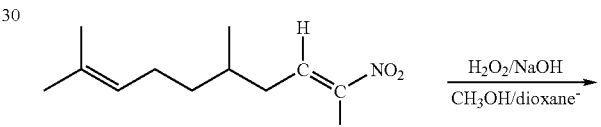

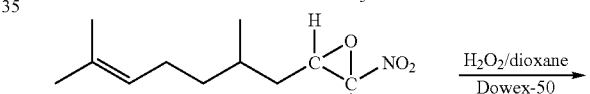

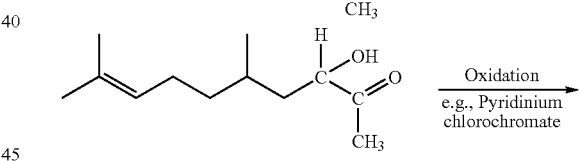

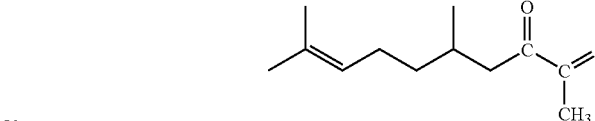

An additional compound that consists of the general formula R—(C=O)—(C=O)—R', or a masked form of such a group as denoted elsewhere in this application (e.g. acetal, ketal, etc.), and is contemplated by this disclosure is the following:

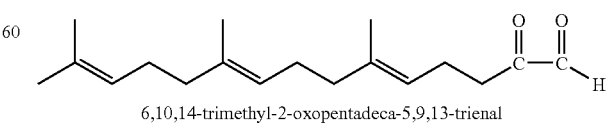

6,10,14-trimethyl-2-oxopentadeca-5,9,13-trienal

The synthesis of the above compound may be carried out according to the following scheme:

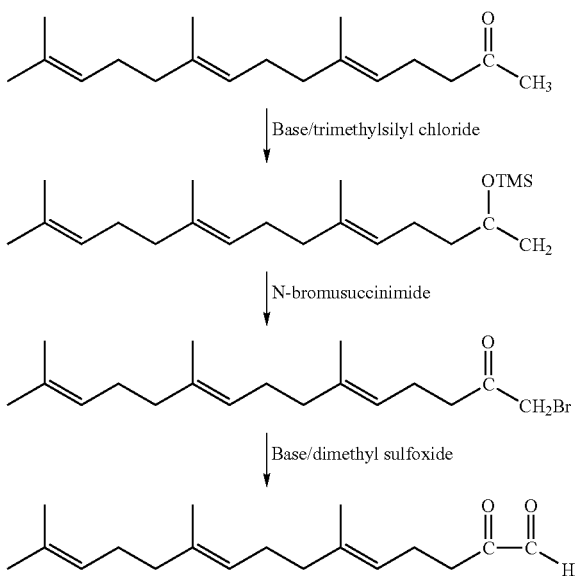

A further example of the class of compounds of the type R—(C=O)—(C=O)—R', or a masked form of such a group as denoted elsewhere in this application (e.g. acetal, ketal, etc.), is exemplified by dehydroascorbic acid 6-palmitate, shown below:

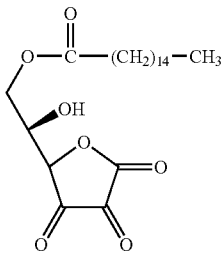

This compound may advantageously be synthesized by oxidation of ascorbic acid 6-palmitate, as follows:

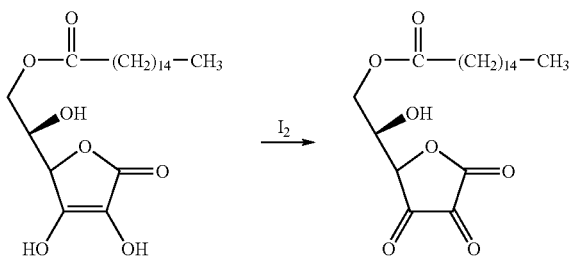

Other embodiments contemplated include compounds in which the —(CH$_2$)$_{14}$CH$_3$ group shown in the structural formula of the 6-palmitate is replaced by a group R as defined elsewhere herein. These include other 6-esters of dehydroascorbic acid, such as dehydroascorbic acid 6-farnesenoate, in which the —(CH$_2$)$_{14}$CH$_3$ group shown in the structural formula of the 6-palmitate is replaced by the —CH=C(CH$_3$)CH$_2$CH$_2$CH=C(CH$_3$)CH$_2$CH$_2$CH=C (CH$_3$)$_2$ group. Dehydroascorbic acid esters contemplated by this disclosure are inclusive of the 5-isomers as well as the 6-isomers.

Some cancer cells in which farnesylation of Ras is blocked employ the related prenylation reaction geranylgeranylation to attach a hydrophobic group to Ras to accomplish membrane localization and continued cancerous behavior of the cell. The enzyme that attaches the geranylgeranyl group to Ras protein to facilitate the latter's localization at the inner surface of the cancer cell membrane is geranylgeranyl protein transferase, also known as protein geranylgeranyltransferase (herein referred to as GGTase). The geranylgeranyl group becomes attached to Ras by reaction with geranylgeranyl diphosphate, also known as geranylgeranyl pyrophosphate (herein referred to as GGPP). In other words, GGTase catalyzes the following reaction, in which Ras becomes attached to the geranylgeranyl group by displacement of pyrophosphate (PP$_i$):

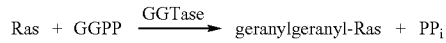

The newly formed geranylgeranyl-Ras localizes at the inner surface of the cancer cell membrane and causes the cancer cell to divide without restraint. Thus, a key target in a strategy to retard cancer cell proliferation is the enzyme GGTase. By reducing or destroying GGTase activity, either in combination with inactivation of Ras farnesylation or independently, we hope to prevent Ras geranylgeranylation, which in turn should prevent localization of Ras at the inner surface of the cancer cell membrane, thereby preventing Ras from causing the cancer cells to divide and proliferate.

Geranylgeranylation of Ras results in the loss from GGPP of pyrophosphate, which is anionic, a process that might be facilitated by a chemical group in GGTase's active site that would favorably interact with pyrophosphate, such as by ionic bonding to a positively charged group like the side chain of arginine [R—NH=C(NH$_2$)$_2^+$]. Thus, chemical reagents that react with the arginine side chain, such as those that possess the functional group consisting of two adjacent carbonyl groups, i.e., O=CC=O, might effectively prevent one or more arginine residues in GGTase from assisting in the pyrophosphate departure, thereby blocking or impeding geranylgeranylation of Ras. Furthermore, to target better the substance to GGTase in preference to other enzymes, and to target better the substance to the active site of GGTase in preference to the external or noncatalytic portion of the enzyme, a preferred embodiment of the invention would consist of a substance with the dicarbonyl functional group and other structural features that would direct or otherwise favor the binding of the agent to the active site of GGTase.

To fine-tune the inactivator to fit the active site of FTase or GGTase, variation of the distance between the arginine-binding end and the farnesyl-mimicking or geranylgeranyl-mimicking end can be achieved through alteration of the length of the spacer, i.e., by variation of "n" from 0 to 10 in the generalized diagram below:

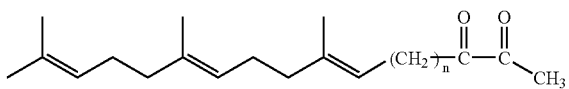

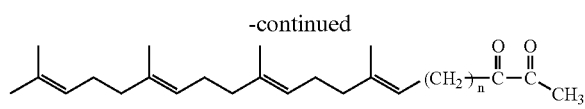

Additional inactivators incorporating aromatic groups for enhanced binding to the hydrophobic binding site of FTase or GGTase are exemplified by the following compound, although there are numerous possible variants of this type of compound (e.g., the location of the aromatic ring and the pattern of substitution as ortho, meta, or para; a heterocyclic ring; a nonaromatic ring; multiple rings; etc.):

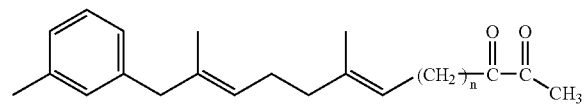

A further embodiment of this invention is based on the observation that there are two arginine residues in the active site of FTase. Because such arginine residues are at a characteristic distance unique to FTase, selective reaction with FTase over other enzymes and proteins can be accomplished by use of a substance in which two dicarbonyl functionalities are separated by a spacer, such substances being represented by the following generalized formula:

D-L-D in which D is a dicarbonyl functional group, O=C—C=O, or a masked form of such a group as denoted elsewhere in this application (e.g. acetal, ketal, etc.), and L is a linker group that is compatible with and/or has an affinity for the prenylation enzyme. One embodiment of this invention, in which two dicarbonyl functional groups are connected via a linker, is 4,4'-biphenyldiglyoxaldehyde, shown below:

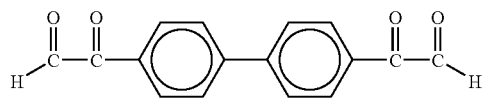

This category of compounds is further exemplified by the bis(α-oxoaldehyde) below:

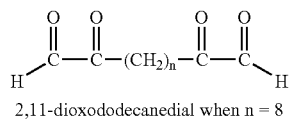

2,11-dioxododecanedial when n = 8

The spacer, $(CH_2)_n$, can be varied in length and in other characteristics (e.g., steric bulk, etc.) to optimize the selectivity for FTase and the ability to block the FTase active site. Alternatives to the bis(α-oxoaldehyde) above include substances of the bis(α-oxoketone) type or compounds with both an α-oxoketone and α-oxoaldehyde functionality, as well as others readily apparent to those skilled in the art, having regard for this disclosure. Thus, reaction of FTase with compounds such as the bis(dicarbonyl) compound shown above might occur with high efficiency and selectivity, and the covalent attachment of such compounds to FTase might be particularly effective at blocking the active site from utilizing the natural substrates FPP and Ras protein, which need to bind to FTase in the vicinity of the two arginine residues.

Another embodiment of the invention utilizes the characteristics of the C-terminus of the Ras protein, i.e., the negative charge, for noncovalent binding to one of the arginine residues and the dicarbonyl functionality for covalent binding to the other arginine residue. The theory has been put forth that one of the arginine residues holds the Ras protein in the active site through electrostatic binding of the arginine residue's positive charge to the carboxyl terminus of Ras protein, which is negatively charged. The other arginine residue binds FPP through the electrostatic attraction of the negative charge of FPP to the positive charge of the arginine side chain. Thus, one such class of compounds that interfere with protein prenylation that is contemplated by this disclosure consists of four-part molecules symbolized as follows:

A-L-D-R in which each part is defined as follows:

A is (1) an anionic group, e.g., carboxylate, sulfate, sulfonate, sulfinate, phosphate, phosphonate, thiophosphate, pyrophosphate, enolate, sulfonamide, sulfone, or tetrazole, (2) a group that can become anionic at physiological pH, e.g. $CO_2H$ by deprotonation, or (3) a group that can be acted upon by an enzyme to reveal a group that can become anionic at physiological pH, e.g. the ester $R'CO_2R$ is hydrolyzed by endogenous esterases to form the acid $R'CO_2H$, which subsequently ionizes at physiological pH to $R'CO_2^-$;

L is a linker group that is compatible with and/or has an affinity for the prenylation enzyme, for example an alkyl, alkenyl, alkynyl, or aryl group.

D is a dicarbonyl functional group (O=C—C=O) or a masked form of such a group as denoted elsewhere in this application (e.g., acetal, ketal, etc.).

R is a group selected from the group consisting of an alkyl, alkenyl, alkynyl, or aryl group.

Specific embodiments of such a four-part molecule are the following camphorquinone sulfonamides:

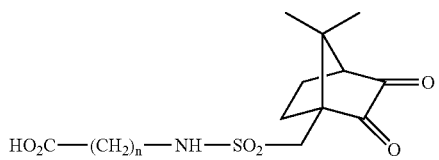

in which n is advantageously equal to 4, 5, 6, or 7, or another value for optimal binding to prenyltransferases. It will be apparent to those skilled in the art and having regard for this disclosure that other linking groups L, other anion-generating or anionic groups A, and other dicarbonyl groups D, or masked forms of such groups as denoted elsewhere in this application (e.g. acetals, ketals, etc.), can be advantageously substituted for the polymethylene chain —$(CH_2)_n$—, carboxyl group, and camphorquinone moiety, respectively, in the above structure. For example, a prodrug, i.e., a substance that has advantages of stability, solubility, cell permeability, etc., but that liberates the active or a more active substance in the living tissues, e.g. spontaneously and/or by action of endogenous enzymes, light, and/or heat, could advantageously be formulated to be the camphorquinone sulfonamide esters represented by the structure shown below:

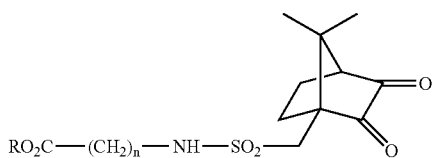

in which R may be any of a very wide variety of groups, such as simple straight-chain, branched, or cyclic and heterocyclic aliphatic groups (including functional groups containing heteroatoms, such as ether linkages, amino and hydroxyl groups), and aromatic groups, including heterocycles.

Both of the enantiomeric camphorquinone sulfonamides (i.e., both (+) and (−) stereoisomers) are contemplated by this patent and might be advantageously used for interference with protein prenylation.

The synthesis of camphorquinone sulfonamides can be carried out as illustrated below:

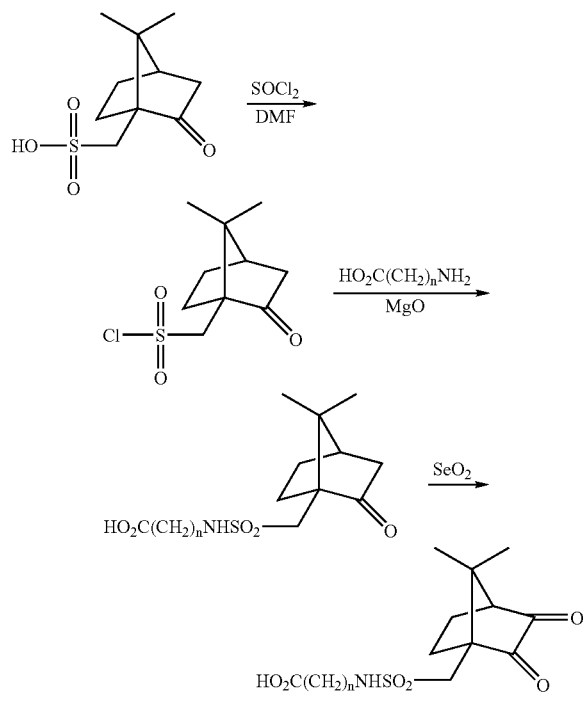

Additionally, the compound below, when in its ionized form (the predominant form present at physiological pH), has the characteristics required for the noncovalent binding of the carboxylate terminus to one arginine residue, and the covalent binding of the dicarbonyl functionality to the other arginine residue:

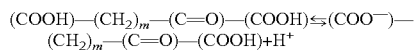

When m=9, the compound is 11,12-dioxododecanoic acid, a preferred compound of the invention. Typically m=1 to 25, more preferably 5-13.

Other embodiments can combine the carboxylic acid group and an α-oxoaldehyde or, alternatively, a carboxylic acid group and an α-oxoketone group within the same molecule, or other combinations that are readily apparent to those skilled in the art, having regard for this disclosure. By modification of the linker group's structure (e.g., length, steric bulk, etc.), the specificity of the compound for FTase and the effectiveness of the compound against FTase can be fine-tuned. Use of known non-covalent inhibitors of FTase and GGTase as linker or R groups is preferred to increase specificity for the enzyme active site.

For example, the tetrapeptide portion of Ras that is recognized by FTase (referred to as CAAX, in which C represents cysteine, A represents an aliphatic amino acid, and X represents a limited subset of the naturally occurring amino acids, of which serine is an example) can be utilized in combination with a dicarbonyl functionality to target the inactivator to its target, FTase. Such a compound might be a useful inactivator. It might, however, be hydrolyzed by cellular proteases, so a peptidomimetic analogue less prone to cellular hydrolysis might show superior lifetime in a cell, thereby enhancing its chances of combining with FTase and inactivating it. An embodiment of a peptidomimetic analogue of the tetrapeptide in which a dicarbonyl functionality is present is shown below:

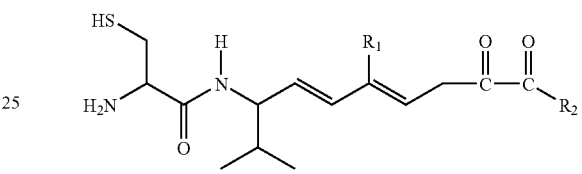

In the structure above, $R_1$ is a substituent suitable for recognition and binding to FTase, and $R_2$ is typically H or $CH_3$, for reaction with an arginine residue in the FTase active site. Many other embodiments of this type are readily apparent to those skilled in the art, having regard for this disclosure.

There are numerous ways to synthesize a-dicarbonyl compounds. One is by oxidation of a monocarbonyl compound with selenium dioxide ($SeO_2$), shown below:

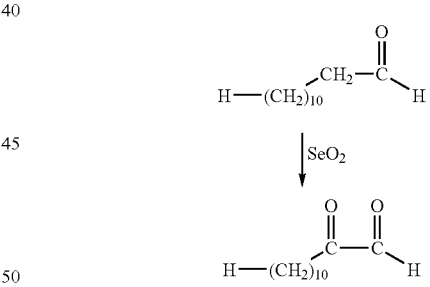

Another method of preparation of α-dicarbonyl compounds is by alkylation of 2,3-butanedione, illustrated below:

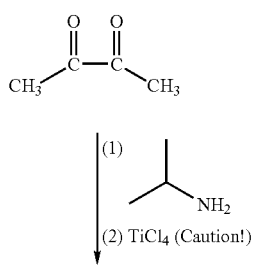

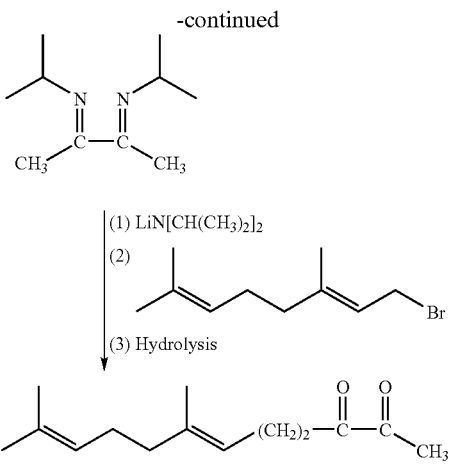

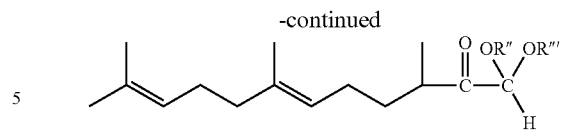

The examples below show that FTase is sensitive to inactivation by phenylglyoxal and by 2-oxododecanal, both of which are α-dicarbonyl compounds. New opportunities exist for the development of -dicarbonyl compounds and related substances that might prove to be inactivators of prenylation enzymes with varying potencies and specificities. A specific protein designated K-Ras is the most common mutant Ras protein found in human cancers. Farnesylation inhibitors, however, cannot prevent cellular prenylation of K-Ras because geranylgeranylation of K-Ras takes place. If GGTase has an active-site arginine, -dicarbonyl compounds like PGO might likewise be effective inactivators of that enzyme as well.

Another means of synthesis of α-dicarbonyl compounds is illustrated below, starting with citronellal:

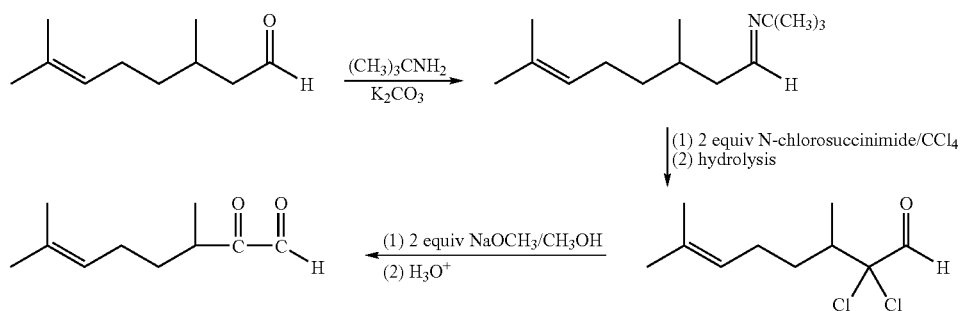

Other embodiments of the invention are substances in which one or more carbonyl groups are masked as a hydrate [C(OH)$_2$], a hemiacetal or hemiketal [C(OH)(OR''')], an acetal or a ketal [C(OR'')(OR''')], an acylal or related compound [C(OC(=O)R'')(OC(=O)R''')], a bisulfite addition compound [C(OH)(SO$_3^-$)], an enol (C=COH), an enol ether (C=COR''), an enol ester [C=COC(=O)R''], and so forth, wherein R'' and R''', which may be the same or different, are alkyl, alkenyl, and/or aryl groups. Such masked carbonyl groups may produce the carbonyl form of the reagent in solution. Acetals and ketals with hydrophobic side chains, including those that resemble the farnesyl group, are shown below:

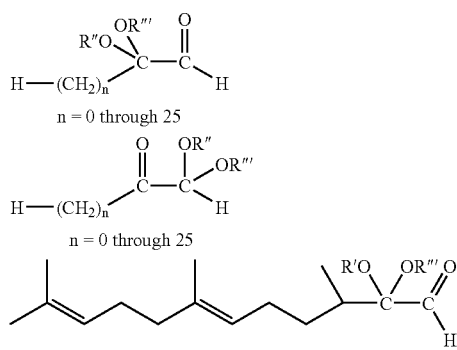

The ability of the α-dicarbonyl functional group to achieve FTase inactivation is described in the examples below, and compounds of this type offer a new approach to the treatment and control of cancer. Suitable levels of enzyme activity reduction range from at least 10% to at least 95% or even 100%. Any level can be selected as desired, using appropriate chemical substitutents to achieve at least 10, 20, 30, 40, 50, 60, 70, 80, or 90% reduction in enzyme activity. Typical routes of administration of these substances that might be suitable for clinical applications are oral and intravenous, although other routes might prove beneficial in specific cancers (e.g., intraperitoneal, intramuscular, subcutaneous, intrathecal, or topical for skin cancers). Doses and frequency of administration are to be selected based upon considerations of beneficial effects (e.g., tumor growth reduction or tumor shrinkage) compared to side effects (e.g., systemic toxicity). Combination with other anticancer agents to produce synergistic effects of benefit to the patient are also possible. Combination therapy might be based on two strategies. One is to interfere with different biochemical processes to increase tumor cell killing. Another is to hamper development of drug resistance, which is less likely to occur simultaneously in tumor cells exposed to anticancer agents based on interference with different biochemical pathways in the tumor cells.

Compounds according to the invention may be purified free of impurities, preferably to a level of at least 50, 70, 90, or 95%. The compounds may be formulated in suitable pharmaceutically acceptable diluents, excipients or carriers. These can provide for additional properties, such as enhanced absorption, slow release, tissue or organ targeting, etc.

In summary an improved method of interference with protein prenylation in tumor cells has been described that may prevent or hamper the proliferation of tumor cells, possibly resulting in a decrease in tumor size and/or disappearance of the cancer.

EXAMPLE 1

An example of an embodiment of this invention is phenylglyoxal monohydrate, shown below, which is in equilibrium with the dicarbonyl form:

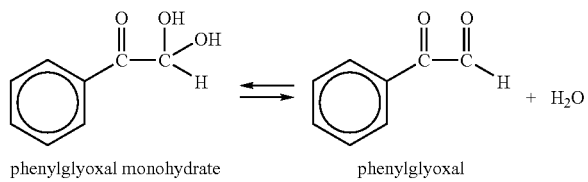

phenylglyoxal monohydrate      phenylglyoxal

The application of phenylglyoxal monohydrate to solutions of FTase resulted in the rapid and virtually complete inactivation of the enzyme in a matter of seconds to minutes, depending upon the concentration of phenylglyoxal monohydrate applied. For example, the catalytic ability of FTase was monitored by an assay procedure in which FTase transferred the farnesyl group from FPP to a peptide substitute for Ras. The peptide substitute for Ras in this assay had structural elements in common with Ras, in particular a sequence of four amino acids cysteinyl-valyl-lysyl-serine (cys-val-lys-ser). In addition the peptide contained an amino acid residue that had a fluorescent marker attached, dansyl-glycine (DNS-gly). Farnesyl group transfer by FTase from FPP to DNS-gly-cys-val-lys-ser resulted in an increase in fluorescence due to the attachment of the hydrophobic group to the cysteine near the dansyl group. Thus, enzyme activity is revealed by an increase in fluorescence of the dansyl group, as shown in the accompanying FIG. 1.

Inactivation of the enzyme FTase occurred when the FTase was preincubated with phenylglyoxal monohydrate, as evidenced by (1) a decrease in enzyme activity with increasing time of preincubation with phenylglyoxal monohydrate; and (2) a decrease in enzyme activity with increasing concentration of phenylglyoxal monohydrate. Because of interference of phenylglyoxal monohydrate with the fluorescence assay used, phenylglyoxal monohydrate was removed from the FTase preincubation mixture by ultrafiltration prior to the assay being performed. The accompanying FIG. 2 shows the loss of activity of FTase due to inactivation by phenylglyoxal monohydrate.

Evidence for the binding of phenylglyoxal in the farnesyl pyrophosphate binding region of the enzyme was obtained by preincubation of the enzyme with farnesyl pyrophosphate, followed by treatment with phenylglyoxal. As shown in the accompanying FIG. 3, higher concentrations of farnesyl pyrophosphate more effectively reduced the inactivation of FTase by phenylglyoxal. This suggests that the farnesyl pyrophosphate bound to and blocked phenylglyoxal from the site of the reaction that brings about inactivation, namely chemical modification of an active-site arginine side chain.

A detailed description of the results summarized above follows. Upon farnesylation by protein farnesyltransferase (FTase),[1] Ras protein becomes localized at the inner surface of the cell membrane. Localization is essential for the mitogenic role of mutant Ras protein, which acts as a switch for cancer cell proliferation. We found that phenylglyoxal (PGO), which is a protein-modification reagent that is specific for arginine, potently obstructs farnesylation of a Ras model peptide by FTase. Covalent modification interferes with catalysis and results in mechanism-based inactivation of FTase. FTase activity in vitro was monitored by a fluorescence assay. FTase was rapidly inactivated by preincubation with PGO. At 20 mM PGO, FTase activity was totally lost within 2 minutes. Inactivation rates at 10 mM PGO and 5 mM PGO were successively slower. Preincubation of FTase with FPP prior to incubation with PGO decreased the ability of PGO to inactivate FTase. These results imply that a bimolecular reaction occurred between PGO and FTase, probably in the vicinity of the FPP binding site, which resulted in the inactivation of the enzyme. These findings reveal the value of -dicarbonyl compounds for mechanistic studies of FTase and for potentially selective regulation of protein farnesylation for possible anticancer chemotherapy.

Posttranslational modification of a small number of proteins is carried out by protein farnesyltransferase (FTase), which attaches the 15-carbon farnesyl group of farnesyl pyrophosphate to the sulfhydryl group of a cysteine residue near the C-terminus of the substrate protein. Noteworthy among the proteins that are substrates for FTase is Ras protein, which upon farnesylation becomes localized at the lipid bilayer of the inner surface of the cell membrane. Localization is essential for the mitogenic role of Ras, which acts as a switch for cell division. Cycling between the inactive form (GDP-bound Ras) and the active form (GTP-bound Ras), is part of the normal mechanism of cell growth regulation.

Mutant forms of Ras protein have lost GTPase activity and trigger unrestrained cell division. Approximately one third of all human cancers exhibit a mutant ras genotype, with substantial variations in the incidence from tumor type to tumor type. This has made blockage of farnesylation of mutant Ras protein an active area of research as it appears that inhibition of both normal and mutant Ras protein farnesylation is more harmful to cancer cells than normal cells. The challenges to this coup de main against cancer, however, are manifold. Some cancer cell lines with mutant ras genotypes are insensitive to FTase inhibitors, and some cancer cell lines without mutant ras genotypes are sensitive to FTase inhibitors. This may mean that a delicate balance between reduction in farnesylation of different proteins is required for effective anticancer strategies. A possible addition to the armamentarium of farnesylation regulators based on a new approach is described in this report.

Recognition of Ras and related protein substrates of FTase is based on a structural motif consisting of a C-terminal CAAX sequence, in which A represents an aliphatic amino acid and X is preferentially serine. The related posttranslational geranylgeranylation, in which the 20-carbon geranylgeranyl chain is attached to the cysteine of CAAX by geranylgeranyltransferase (GGTase), occurs preferentially when X is methionine.

Nucleophilic attack by the cysteine sulfhydryl group of CAAX, activated by an enzyme-bound zinc ion, results in Ras farnesylation, with departure of pyrophosphate from FPP. We surmised that catalysis of farnesylation by FTase might be facilitated by salt-bridge formation (i.e., electrostatic stabilization) between the pyrophosphate leaving group of farnesyl pyrophosphate and a cationic amino acid side chain such as the guanidinium group of arginine. This speculation was strengthened by the recent publication of some aspects of FTase structure obtained from X-ray crystallographic analyses. An arginine ($Arg^{291}$) was found to be in close proximity to the binding site of the diphosphate portion of FPP and the active-site zinc ion, near the upper part of the barrel-shaped active site. Another key arginine in the bottom of the active site, $Arg^{202}$, is proposed to form a salt bridge with the carboxyl group of the CAAX terminus of the Ras peptide substrate. In addition the aliphatic part of the arginine side chain is buttressed with the FPP aliphatic chain. FTase's preference for FPP relative to GGPP can be understood because the latter would project from the cleft and be poorly positioned for transfer of the geranylgeranyl group to the protein substrates of FTase.

We report herein that a protein-modification agent, phenylglyoxal, that is specific for the arginine side chain potently obstructs farnesylation of a Ras model peptide by FTase. This approach of specific covalent modification of FTase to interfere with catalysis results in mechanism-based inactivation of FTase, in contrast to the numerous noncovalent inhibitors that have been identified. Covalent modification is in principle virtually irreversible and might be tailored to active site residues of FTase. Inactivation thus opens the door to mechanistic studies and potentially selective obstruction of FTase and/or GGTase for possible anticancer chemotherapeutic benefit.

Experimental Procedures:

Materials. All reagents were from Sigma Chemical Co. and used without further purification, except as noted.

Purification of PGO—PGO (Aldrich Chemical Co.) was dissolved in boiling water that contained charcoal, and the mixture was gravity filtered through Celite while hot. Upon cooling, the solution was filtered by suction to obtain the PGO, and the PGO was repeatedly recrystallized from water until its $^1$H NMR spectrum and melting point indicated the absence of impurities, such as polymeric material. All PGO solutions were freshly prepared before use in the studies described below.

Preparation of Ds-GCVLS Ds-GCVLS was prepared by a method analogous to a published procedure. Synthesis was performed by use of a Millipore 9050 Plus PepSynthesizer that employed standard Fmoc solid phase peptide synthesis methodology. PS-PEG resin and Fmoc protected amino acids were obtained from Millipore. The N-dansylglycine was from Sigma Chemical Co. Peptide purification was performed by RP-HPLC on an Alltech Macrosphere RP300 C8 column. Elution was accomplished with a linear gradient from aqueous 10 mM trifluoroacetic acid to 10 mM trifluoroacetic acid in acetonitrile. Lyophilization yielded a pale yellow solid. Stock solutions were prepared in 50 mM Tris containing 5 mM DTT and 0.2% n-octyl-β-D-glucopyranoside (Anatrace, Inc.), pH 7.7. Concentrations of Ds-GCVLS were determined by use of the extinction coefficient of the dansyl group at 340 nm (=4250 $M^{-1}$ $cm^{-}_1$). Stock solutions were stored at −20 C. FTase (stored at −70 C) was a generous gift from Professor Patrick Casey at Duke University.

FTase assay The fluoresence assay conditions were adapted from a published method. The FTase assay consisted of the measurement of the rate of FTase-catalyzed farnesylation of the fluorescent pentapeptide Ds-GCVLS. Upon farnesylation of the cysteine, the fluoresence emission at =505 nm of the dansyl group is enhanced due to the proximity of the hydrophobic isoprenoid group. Enzyme activity (approximately 60 nM FTase) was monitored at saturating substrate concentrations (10 M farnesyl pyrophosphate, ammonium salt, prepared by successive dilutions of a commercial 2.3 mM solution in methanol:10 mM aqueous $NH_4OH$ (7:3) into assay buffer, and 1.0 M Ds-GCVLS) by measurement of the increase in fluorescence emission observed at =505 nm as FTase farnesylated Ds-GCVLS for a period of 10 min. The assay buffer was selected for unreactivity toward PGO: 50 mM NaHEPES, 5 mM DTT, 5 mM $MgCl_2$, 10 μM $ZnCl_2$, and 0.2% n-octyl-β-D-glucopyranoside, pH 7.5. Fluorescence emission was measured with a JASCO FP-77 spectrofluorimeter fitted with a temperature-controlled cuvette holder connected to a 30 C. constant temperature bath. All fluoresence assays were conducted in a 4 mm 4 mm quartz cuvette with excitation at 340 nm.

Inactivation of FTase by PGO FTase was incubated at 30 C in the presence and absence of PGO at various concentrations in 50 mM NaHEPES, 5 mM $MgCl_2$, 10 μM $ZnCl_2$, and 0.2% n-octyl-β-D-glucopyranoside, pH 7.5 (i.e., assay buffer without DTT). Periodically, aliquots of the FTase-PGO reaction mixture were removed and assayed for FTase activity. Because of interference of PGO with the fluorometric assay, the aliquot was first subjected to solvent exchange by size exclusion membrane concentration to remove PGO. The solvent exchange utilized Microcon (Millipore Co.) 30 kD molecular weight cutoff microconcentrators. This also served to stop further inactivation of the enzyme by PGO. A 100-L aliquot of FTase-PGO reaction mixture was pipetted into a Microcon concentrator, which was centrifuged at 12,000 RPM for 8 min at 4 C. The concentrate was resuspended in 100 L of assay buffer, and centrifugation was repeated. The final concentrate was resuspended in 90 L of assay buffer, and the resulting solution was recovered by inversion of the concentrator and centrifugation at 3500 RPM for 3 min at 4 C. The solution was then assayed for FTase activity as described above. A control was handled as above, except that PGO was omitted from the incubation mixture.

FPP protection of FTase against inactivation by PGO FTase was treated with FPP at various concentrations in assay buffer without DTT for 2 min at 30° C. prior to incubation of the mixture with 10 mM PGO for 30 min at 30° C. The control was incubated with FPP at the corresponding concentration for the full length of time, but without PGO. The mixtures were subsequently subjected to microconcentration and assay, as described above.

Results and Discussion:

FTase activity in vitro was monitored by a fluorescence assay, shown in FIG. 1, in which activity was determined from the initial slope of a plot of the fluorescence increase vs. time. FTase was rapidly inactivated by preincubation with PGO, as shown in FIG. 2. At 20 mM PGO, FTase activity was totally lost before the first assay at 2 minutes after mixing of PGO and FTase (data not shown). Inactivation by 10 mM PGO was slower but still quite rapid. At 5 mM PGO the rate of inactivation was reduced. These results imply that a bimolecular reaction occurred between PGO and FTase, which resulted in the inactivation of the enzyme.

Inactivation kinetics differ from inhibition kinetics. Inactivation kinetics typically consist of the bimolecular conversion of the active form of the enzyme (E) into impaired and/or completely inactive form(s) of the enzyme (E'), as shown in the equation below, where PGO is the inactivator:

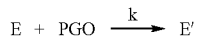

Because the inactivator is typically present in large excess over the enzyme and therefore remains at essentially constant concentration, disappearance of enzyme activity follows pseudo-first-order kinetics, described by the following equation:

$$[E]_t/[E]_0 = \exp(-k[PGO]t)$$

in which $[E]_t$ is the enzyme concentration or activity remaining at time t, $[E]_0$ is the initial enzyme concentration or activity, and [PGO] is the concentration of PGO. Thus, a plot of log $[E]_t/[E]_0$, i.e., log (fraction of activity remaining), versus time is expected to be linear, with a slope of k[PGO]/2.303. Thus, the time-dependence and inhibitor-concentration-dependence of loss of enzyme activity are indicative of inactivation of the enzyme.

Previously, the stepwise formation of a 2:1 PGO-enzyme adduct has been seen kinetically as a biphasic time course of inactivation of porcine liver prenyltransferase, presumably due to rapid, reversible 1:1 adduct formation resulting in reduced activity of the enzyme, followed by slower, irreversible 2:1 adduct formation, and conversion of the enzyme into a less active form. Some indication of similar behavior is seen in FIG. 2, especially at low PGO concentration.

Preincubation of FTase with FPP prior to incubation with PGO decreased the ability of PGO to inactivate FTase, as shown in FIG. 3. This implies that an active site arginine residue is the principal site of the reaction with PGO that inactivates the enzyme. When arginine modification occurs in the FPP binding site, then obstruction of subsequent binding of FPP would be expected to prevent farnesylation of the substrate pentapeptide. The low concentration of PGO required for inactivation of the enzyme is also consistent with the idea that specific modification of an active-site arginine has occurred.

It is not possible to rule out that the arginine side-chain modification results in destruction of the catalytic ability of the active-site arginine without blockage of FPP binding. Likewise, some modification of lysine side chains and -amino groups is possible with phenylglyoxal, although under the short incubation times used in these studies, such modification would be expected to be of minor importance. Destruction of enzyme activity by modification of numerous arginines, which might for example lead to gross conformational changes and concomitant loss of catalytic ability, also would not be expected to occur under these conditions. In either case, the observed protective effect of FPP would not necessarily have been expected. Future studies, however, are required to establish whether $Arg^{291}$ is the principal site of modification of FTase by PGO. Such studies will also ascertain whether another amino acid is a significant target of PGO modification.

EXAMPLE 2

In the same manner as Example 1, compound 2-oxododecanal was tested for inactivation of FTase in the fluorescence assay system described, except as noted below. Final concentrations in the incubation mixture were 5, 10, and 35 mM 2-oxododecanal. A stock solution of 2-oxododecanal dissolved in dimethyl sulfoxide (DMSO) was employed. The final concentration of DMSO in the incubation mixture (as well as the control) was 5%. The results are shown in FIG. 4. It was found that 2-oxododecanal rapidly inactivated FTase, probably by reaction with one or both of the active site arginine residues. This would block access of one or both of the substrates (FPP and/or the peptide substitute for Ras protein) and/or block the catalytic function of one or both of the arginine residues, resulting in inactivation of the enzyme.

EXAMPLE 3

In the same manner as EXAMPLE 1, compound 5,9-dimethyl-8-decene-2,3-dione was tested for inactivation of FTase in the fluorescence assay system described, except as noted below. A stock solution of 5,9-dimethyl-8-decene-2,3-dione in 5% DMSO was employed. The final concentration of DMSO in the incubation mixture (as well as the control) was 4.6%. FTase was at 15 nM, and the Microcon concentration step was omitted. It was found that 5,9-dimethyl-8-decene-2,3-dione rapidly inactivated FTase. After 30 minutes of incubation with 17, 68, or 171 μM 5,9-dimethyl-8-decene-2,3-dione, FTase activity was reduced to 38%, 18%, or 16% of the initial control value, respectively.

EXAMPLE 4

In the same manner as EXAMPLE 1, dehydroascorbic acid 6-palmitate was tested for inactivation of FTase in the fluorescence assay system described, except as noted below. A stock solution of dehydroascorbic acid 6-palmitate in 2% DMSO in 5 mM sodium acetate, pH 3.9, was employed. The final concentration of DMSO in the incubation mixture (as well as the control) was 0.46%. FTase was at 15 nM, and the Microcon concentration step was omitted. It was found that dehydroascorbic acid 6-palmitate rapidly inactivated FTase. After 30 minutes of incubation with 7, 28, or 141 μM dehydroascorbic acid 6-palmitate, FTase activity was reduced to 75%, 34%, or 22% of the initial control value, respectively.

EXAMPLE 5

In the same manner as EXAMPLE 1, compound 4,4'-biphenyldiglyoxaldehyde was tested for inactivation of FTase in the fluorescence assay system described, except as noted below. A stock solution of 4,4'-biphenyldiglyoxaldehyde in 5% DMSO was employed. The final concentration of DMSO in the incubation mixture (as well as the control) was 4.6%, and FTase was at 15 nM. It was found that 4,4'-biphenyldiglyoxaldehyde rapidly inactivated FTase. After 30 minutes of incubation with 23 or 93 μM 4,4'-biphenyldiglyoxaldehyde, FTase activity was reduced to 68% or 11% of the initial control value, respectively.

EXAMPLE 6

As a test of the importance of the presence of a dicarbonyl functional group, a compound analogous to that used in EXAMPLE 5 but without such a group was tested. Thus, in the same manner as EXAMPLE 1, compound 4,4'-diacetylbiphenyl, whose structure is as follows:

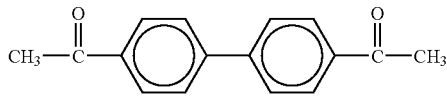

was tested for inactivation of FTase in the fluorescence assay system described, except as noted below. A stock solution of 4,4'-diacetylbiphenyl in 5% DMSO was employed. The final concentration of DMSO in the incubation mixture (as well as the control) was 4.6%, FTase was at 15 nM. It was found that 4,4'-diacetylbiphenyl did not inactivated FTase. Even after 120 minutes of incubation with 23 μM 4,4'-diacetylbiphenyl, FTase activity was the same as the control, within experimental error.

EXAMPLE 7

In the same manner as EXAMPLE 1, compound 2,3-pentanedione, $CH_3CH_2(C=O)-(C=O)CH_3$, was tested for inactivation of FTase in the fluorescence assay system described, except as noted below. The assay was carried out in the presence of 50 mM sodium borate, pH 7.5. FTase was at 15 nM, and the Microcon concentration step was omitted. It was found that 2,3-pentanedione rapidly inactivated FTase. After approximately 30 minutes of incubation with 17, 33, or 66 mM 2,3-pentanedione, FTase activity was reduced to 69%, 55%, or 37% of the initial control value, respectively.

Footnotes:
[1]The abbreviations used are: Ds-GCVLS, the dansyl-labeled pentapeptide N-dimethylaminonaphthalene-sulfonyl-Gly-Cys-Val-Leu-Ser; DTT, dithiothreitol; Fmoc, 9-fluorenylmethoxycarbonyl; FTase, human recombinant protein farnesyltransferase; FPP, farnesyl pyrophosphate; GGPP, geranylgeranyl pyrophosphate; GGTase, protein geranylgeranyltransferase; HEPES, N-2-hydroxyethylpiperazine-N-2-ethanesulfonic acid; PGO, phenylglyoxal monohydrate; Tris, tris(hydroxymethyl)aminomethane.

REFERENCES

1. Casey, P. J. (1992) *J. Lipid Res.* 33, 1731-1740.
2. Bos, J. L. (1989) *Cancer Res.* 49, 4682-4689.
3. Casey, P. J. and Seabra, M. C. (1996) *J. Biol. Chem.* 271, 5289-5292.
4. Leonard, D. M. (1997) *J. Med. Chem.* 40, 2971-2990.
5. Gibbs, J. B. and Oliff, A. (1997) *Annu. Rev. Pharmacol. Toxicol.* 37, 143-166.
6. Cassidy, P. B. and Poulter, C. D. (1996) *J. Am. Chem. Soc.* 118, 8761-8762.
7. Patel, D. V., Young, M. G., Robinson, S. P., Hunihan, L., Dean, B. J., and Gordon, E. M. (1996) *J. Med. Chem.* 39, 4197-4210.
8. Sattler, I. And Tamanoi, F. (1996) "Prenylation of RAS and Inhibitors of Prenyltransferases." In *Regulation of the RAS Signaling Network*, H. Maruta and A. W. Burgess, eds., Chapter 4, Chapman & Halkl, Austin, Tex.
9. Huang, C.-C., Casey, P. J., and Fierke, C. A. (1997) *J. Biol. Chem.* 272, 20-23.
10. Dolence, J. M., Cassidy, P. B., Mathis, J. R., and Poulter, C. D. (1996) *Biochemistry* 34 16687-16694.
11. Mu, Y. Q., Omer, C. A., and Gibbs, R. A. (1996) *J. Am. Chem. Soc.* 118, 1817-1823.
12. Park, H.-W., Boduluri, S. R., Moomaw, J. F., Casey, P. J., and Beeese, L. S. (1997) *Science* 275, 1800-1804; Dunten, P., Kammlott, U., Crowther, R., Weber, D., Palermo, R., and Birktoft, J. (1998) *Biochemistry* 37, 7907-7912; Long, S. B., Casey, P. J, and Beese, L. S. (1998) *Biochemistry* 37, 9612-9618.
13. Takahashi, K. (1968) *J. Biol. Chem.* 243, 6171-6179.
14. Boivin, D., Lin, W., and Beliveau, R. (1997) *Biochem. Cell Biol.* 75, 63-69.
15. Barnard, G. F. and Popjak, G. (1980) *Biochim. Biophys. Acta* 617, 169-182.
16. Pompliano, D. L., Gomez, R. P., and Anthony, N. J. (1992) *J. Am. Chem. Soc.* 114, 7945-7946.
17. Patthy, L. And Thesz, J. (1980) *Eur. J. Biochem.* 105, 387-393.
18. Rowell, C. A., Kowalczyk, J. J., Lewis, M. D., and Garcia, A. M. (1997) *J. Biol. Chem.* 272, 14093-14097.
19. Whyte, D. B., Kirschmeier, P., Hockenberry, T. N., Nunez-Oliva, I., James, L., Catino, J. J., Bishop, W. R., and Pai, J.-K. (1997) *J. Biol. Chem.* 272, 14459-14464.

We claim:

1. A method of reducing the activity of a prenylation enzyme, comprising the step of:
   contacting a prenylation enzyme with an α-dicarbonyl compound having a formula:

R1-(C=O)-(C=O)-L-(C=O)-(C=O)-R2 wherein R1 and R2 are independently selected from the group consisting of hydrogen, alkyl, alkenyl, alkynyl, and aryl; and wherein L is selected from the group consisting of alkyl, alkenyl, alkynyl, and aryl whereby the activity of the prenylation enzyme is reduced by at least 50%.

2. The method of claim 1 wherein the activity of the prenylation enzyme is reduced by at least 75%.

3. The method of claim 1 wherein the activity of the prenylation enzyme is reduced by at least 90%.

4. The method of claim 1 wherein the activity of the prenylation enzyme is reduced by at least 95%.

5. The method of claim 1 wherein the α-dicarbonyl compound is a bis(α-oxoaldehyde).

6. The method of claim 1 wherein the α-dicarbonyl compound is 2,11-dioxododecanedial.

7. The method of claim 1 wherein the α-dicarbonyl compound is 4,4'-biphenyldiglyoxaldehyde.

8. The method of claim 1 wherein R1=H.

9. The method of claim 1 wherein R1=CH3.

10. The method of claim 8 wherein R2=H—$(CH_2)_m$- wherein m=0-25.

11. The method of claim 9 wherein R2=H—$(CH_2)_m$- wherein m=0-25.

12. The method of claim 8 wherein L=—$(CH_2)_n$— and n=1-10.

13. The method of claim 9 wherein L=—$(CH_2)_n$— and n=1-15.

14. The method of claim 8 wherein L=—$(CH_2)_n$— and n=10.

15. The method of claim 9 wherein L=—$(CH_2)_n$— and n=11.

16. The method of claim 8 wherein R2 is a linear alkene.

17. The method of claim 9 wherein R2 is a branched alkene.

18. The method of claim 1 wherein the prenylation enzyme is in a cell-free system.

19. The method of claim 1 wherein the enzyme is in a neoplastic cell.

20. A method of screening compounds as anti-tumor agents comprising:

contacting a test compound with a prenylation enzyme, wherein the test compound has a formula:

R1-(C=O)-(C=O)-L-(C=O)-(C=O)-R2 wherein R1 and R2 are independently selected from the group consisting of hydrogen, alkyl, alkenyl, alkynyl, and aryl; and wherein L is selected from the group consisting of alkyl, alkenyl, alkynyl, and aryl; and measuring prenylation activity of the enzyme, wherein a test compound which reduces prenylation activity of at least 50% is a candidate anti-tumor agent.

21. The method of claim 20 wherein the activity of prenylation enzyme is reduced by at least 75%.

22. The method of claim 20 wherein the activity of the prenylation enzyme is reduced by at least 90%.

23. The method of claim 20 wherein the activity of the prenylation enzyme is reduced by at least 95%.

24. The method of claim 20 wherein the prenylation enzyme is in a cell-free system when contacted with the test compound.

25. The method of claim 20 wherein the enzyme is in a neoplastic cell when contacted with the test compound.

26. The method of claim 20 wherein a natural substrate of the enzyme is added to compete with the test compound, wherein such competition indicates specificity of the test compound for the prenylation enzyme.

27. The method of claim 20 wherein the prenylation enzyme is protein farnesyl transferase (FTase).

28. The method of claim 20 wherein the prenylation enzyme is protein geranylgeranyl transferase (GGTase).

29. The method of claim 26 wherein the natural substrate is farnesyl pyrophosphate.

30. The method of claim 26 wherein the natural substrate is geranylgeranyl pyrophosphate.

31. A method of inhibiting the growth of a cancer cell, comprising the step of:

contacting a cancer cell with α-dicarbonyl compound having a formula:

R1-(C=O)-(C=O)-L-(C=O)-(C=O)-R2 wherein R1 and R2 are independently selected from the group consisting of hydrogen, alkyl, alkenyl, alkynyl, and aryl; and wherein L is selected from the group consisting of alkyl, alkenyl, alkynyl, and aryl; whereby the growth of the cancer cell is inhibited.

* * * * *